{ | United States Patent [19] | Missbach }

Patent Number: 5,344,842
Date of Patent: Sep. 6, 1994

[54] THIOSEMICARBAZONE DERIVATIVES

[75] Inventor: Martin Missbach, Rheinfelden, Switzerland

[73] Assignee: Ciba-Geigy Corportion, Ardsley, N.Y.

[21] Appl. No.: 66,815

[22] Filed: May 24, 1993

[30] Foreign Application Priority Data

Jun. 3, 1992 [CH] Switzerland ............ 1778/92
Jun. 3, 1992 [CH] Switzerland ............ 1779/92
Oct. 6, 1992 [CH] Switzerland ............ 3114/92

[51] Int. Cl.$^5$ ............ A61K 31/425; C07D 277/50
[52] U.S. Cl. ............ 514/342; 548/147; 548/194; 546/280; 514/369
[58] Field of Search ............ 548/147, 194; 514/369, 514/342; 546/280

[56] References Cited

U.S. PATENT DOCUMENTS

| | | | |
|---|---|---|---|
| 3,674,780 | 7/1972 | Berkelhammer et al. | 548/194 |
| 3,699,116 | 10/1972 | Meisels et al. | 548/194 |
| 4,489,069 | 12/1984 | Storni | 548/183 |
| 4,697,020 | 9/1987 | Storni et al. | 548/184 |
| 5,229,405 | 7/1992 | Feige et al. | 514/369 |

FOREIGN PATENT DOCUMENTS 0508955 10/1992 European Pat. Off. .
1325061  8/1973 United Kingdom .

OTHER PUBLICATIONS

Chem. Abstr., vol. 61, No. 10, Nov. 9, 1964, No. 12007g–12008a Japan 10,345 (1964), 2,4–Thiazolidinedione derivatives, Hashimoto.

*Primary Examiner*—Joseph Paul Brust
*Assistant Examiner*—Mary Susan H. Gabilan
*Attorney, Agent, or Firm*—Irving M. Fishman; Karen G. Kaiser

[57] ABSTRACT

The invention relates to novel thiosemicarbazones of formula I wherein
  $R_1$ is lower alkyl, lower alk-2-en-1-yl or lower alk-2-yn-1-yl,
  $R_2$ and $R_3$ independently of one another are hydrogen or lower alkyl, or $R_2$ and $R_3$ together are lower alkylidene,
  $R_4$ is hydrogen, lower alkyl, lower alkoxy, aryl or aryl-lower alkyl, or the group —C(=O)—$R_6$ wherein $R_6$ is lower alkyl, aryl, heteroaryl, aryloxy, aryl-lower alkoxy or lower alk-2-en-1-yloxy,
  $R_5$ is aryl, aryl-lower alkyl, unsaturated or saturated heterocyclyl-lower alkyl, lower alkoxycarbonyl-lower alkyl or the group —C(=O)—$R_7$ wherein $R_7$ is lower alkyl, aryl, aryl-lower alkyl, aryl-lower alkenyl, heteroaryl, aryloxy, aryl-lower alkoxy or lower alk-2-en-1-yloxy, or, when $R_4$ is other than hydrogen, $R_5$ may also be lower alkyl, lower alk-2-en-1-yl or lower alk-2-yn-1-yl, and to the salts thereof, to processes for the preparation of the said compounds, to pharmaceutical compositions comprising them and to their use as active ingredients in medicaments.

9 Claims, No Drawings

THIOSEMICARBAZONE DERIVATIVES

The invention relates to novel thiosemicarbazones of formula I

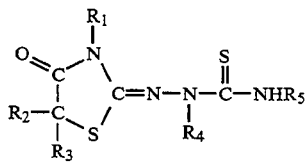

wherein $R_1$ is lower alkyl, lower alk-2-en-1-yl or lower alk-2-yn-1-yl, $R_2$ and $R_3$ independently of one another are hydrogen or lower alkyl, or $R_2$ and $R_3$ together are lower alkylidene, $R_4$ is hydrogen, lower alkyl, lower alkoxy, aryl, aryl-lower alkyl or the group —C(=O)—$R_6$ wherein $R_6$ is lower alkyl, aryl, heteroaryl, aryloxy, aryl-lower alkoxy or lower alk-2-en-1-yloxy, $R_5$ is aryl, aryl-lower alkyl, unsaturated or saturated heterocyclyl-lower alkyl, lower alkoxycarbonyl-lower alkyl or the group —C(=O)—$R_7$ wherein $R_7$ is lower alkyl, aryl, aryl-lower alkyl, aryl-lower alkenyl, heteroaryl, aryloxy, aryl-lower alkoxy or lower alk-2-en-1-yloxy, or, when $R_4$ is other than hydrogen, $R_5$ may also be lower alkyl, lower alk-2-en-1-yl or lower alk-2-yn-1-yl, and to the salts thereof, to processes for the preparation of the said compounds, to pharmaceutical compositions comprising them and to their use as active ingredients in medicaments.

Hereinbefore and hereinafter, "lower" radicals and compounds are to be understood as being, for example, those having up to and including 7, preferably up to and including 4, carbon atoms (C atoms).

Lower alk-2-en-1-yl is, for example, $C_3$-$C_5$alk-2-en-1-yl, such as especially allyl or methallyl.

Lower alk-2-yn-1-yl is, for example, $C_3$-$C_5$alk-2-yn-1-yl, such as especially prop-2-yn-1-yl or but-2-yn-1-yl.

Lower alkyl is, for example, $C_1$-$C_4$alkyl, such as methyl, ethyl, propyl or butyl.

Lower alkylidene is, for example, $C_1$-$C_4$alkylidene, such as especially methylene or ethylidene.

Lower alkoxy is, for example, n-propoxy, isopropoxy, n-butoxy or tert-butoxy, preferably ethoxy and especially methoxy.

Aryl—by itself and also in combined terms such as aryl-lower alkyl—is, for example, phenyl or naphthyl, such as 1- or 2-naphthyl, or substituted phenyl or naphthyl, such as phenyl or naphthyl substituted by lower alkyl, hydroxy-lower alkyl, halo-lower alkyl, hydroxy, lower alkoxy, lower alkanoyloxy, halogen, cyano and-/or by nitro. Aryl is preferably phenyl that is unsubstituted or substituted as indicated above, and is especially phenyl.

Aryl-lower alkyl is preferably phenyl-lower alkyl and especially benzyl.

Aryl-lower alkenyl is preferably phenyl-lower alkenyl, especially phenylallyl or phenylvinyl (phenylethylene).

Aryloxy is, for example, phenoxy.

Aryl-lower alkoxy is, for example, phenyl-$C_1$-$C_4$alkoxy, especially benzyloxy.

Lower alk-2-en-1-yloxy is, for example, $C_3$-$C_5$alk-2-en-1-yloxy, such as especially allyloxy or methallyloxy.

Lower alkoxycarbonyl-lower alkyl is, for example, methoxycarbonyl- or ethoxycarbonylmethyl or -ethyl.

Unsaturated heterocyclyl-lower alkyl is, for example, heteroaryl-lower alkyl.

In combined terms such as heteroaryl-lower alkyl, heteroaryl is to be understood as being an especially monocyclic, but also bi- or poly-cyclic, heterocyclic radical of aromatic character. Bi- and poly-cyclic heteroaryl may be composed of several heterocyclic rings or, preferably, may consist of one heterocycle and one or more, for example one or two and especially one, annellated carbocyclic ring(s), especially benzo ring(s). Each individual ring contains, for example, 3, 5, 6 or 7, and especially 5 or 6, ring members. Heteroaryl is especially an aza-, thia-, oxa-, thiaza-, thiadiaza-, oxaza-, diaza-, triaza- or tetraza-cyclic radical.

Heteroaryl is especially a monocyclic monoaza-, monothia- or monooxa-cyclic radical, such as pyrryl, for example 2-pyrryl or 3-pyrryl, pyridyl, for example 2-, 3- or 4-pyridyl, thienyl, for example 2- or 3-thienyl, or furyl, for example 2-furyl; a bicyclic monoaza-, monooxao or monothia-cyclic radical, such as indolyl, for example 2- or 3oindolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl; a monocyclic diaza-, triaza-, tetraza-, oxaza-, thiaza- or thiadiaza-cyclic radical, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3- or 4-isoxazolyl, thiazolyl, for example 2-thiazolyl, isothiazolyl, for example 3- or 42isothiazolyl or 1,2,4- or 1,3,4-thiadiazolyl, for example 1,2,4-thiadiazol-3-yl or 1,3,4-thiadiazol-2-yl; or a bicyclic diaza-, oxaza- or thiaza-cyclic radical, such as benzimidazolyl, for example 2-benzimidazolyl, benzoxazolyl, for example 2-benzoxazolyl, or benzothiazolyl, for example 2-benzothiazolyl.

Heteroaryl radicals are unsubstituted or carry substituents. Suitable substituents at ring carbon atoms are, for example, the substituents indicated above for aryl radicals and in addition oxo(=O). Ring nitrogen atoms can be substituted, for example, by lower alkyl, aryl-lower alkyl, lower alkanoyl, benzoyl, carboxy, lower alkoxycarbonyl, hydroxy, lower alkoxy, lower alkanoyloxy or by oxido (—O̱).

Heteroaryl is most especially pyridyl, thienyl, pyrryl or furyl.

Heteroaryl-lower alkyl is most especially pyfidyl-, thienyl-, pyrryl- or furyl-methyl. Saturated heterocyclyl-lower alkyl contains a 5- or 6-membered saturated heterocyclic ring having a nitrogen atom or an oxygen atom and is especially an aza- or oxa-cyclic radical which may be unsubstituted or substituted. A saturated 6-membercd heterocyclic ring may also contain a nitrogen atom in addition to an oxygen atom. A saturated 5- or 6-membered heterocyclic ring is, for example, pyrrolidinyl, piperidino, piperidyl, tetrahydrofuranyl or tetrahydropyranyl, wherein one or more hydrogen atoms may have been replaced by one or more substituents, for example by lower alkyl. A saturated 6-membered heterocyclic radical that contains a nitrogen atom in addition to an oxygen atom is, for example, morpholino or morpholinyl. Saturated heterocyclyl-lower alkyl is most especially pyrrolidinyl-, tetrahydrofuranyl- or tetrahydropyranyl-methyl.

Pharmaceutically acceptable acid addition salts of compounds of formula I are, for example, the pharmaceutically acceptable salts thereof with suitable mineral acids, such as hydrohalic acids, sulfuric acid or phosphoric acid, for example hydrochlorides, hydrobromides, sulfates, hydrogen sulfatcs or phosphates, salts with suitable aliphatic or aromatic sulfonic acids or N-substituted sulfamic acids, for example methanesulfonates, benzenesulfonates, p-toluenesulfonates or N-cyclohcxylsulfamates (cyclamates), or salts with strong organic carboxylic acids, such as lower alkanecarboxylic acids or saturated or unsaturated or hydroxylated aliphatic dicarboxylic acids, for example acetates, oxalates, malonates, malcinates, fumaratcs, maleams, tartrates or citrates. Salts of compounds of formula I arc, for example, the acid addition salts thereof, for example the pharmaceutically acceptable salts thereof with suitable mineral acids, such as hydrohalic acids, sulfuric acid or phosphoric acid, for example hydrochlorides, hydrobromides, sulfates, hydrogen sulfates or phosphates, or salts with suitable aliphatic or aromatic sulfonic acids or N-substituted sulfamic acids, for example methanesulfonates, benzenesulfonates, p-toluenesulfonates or N-cyclohexylsulfamates (cyclamates).

The compounds of formula I and the pharmaceutically acceptable salts thereof have valuable pharmacological properties. They have, especially, pronounced anti-arthritic properties. Those properties can be demonstrated in vivo for example using the model of adjuvant arthritis in the rat in accordance with I. Wiesenberg et al., Clin. Exp. Immunol. 78,245 (1989) in a dosage range of from about 0.1 to about 10.0 mg/kg p.o. or i.p., especially from about 0.1 to about 3.0 mg/kg p.o. or i.p..

The compounds of formula I and their pharmaceutically acceptable salts can therefore be used for the treatment of diseases of the rheumatoid type. Those include especially rheumatoid arthritis, juvenile arthritis, ankylosing spondylitis and other seronegative spondylarthritises, for example spondylarthritis in ulcerative colitis and Crohn's disease, and also forms of reactive arthritises, collagen diseases, such as lupus erythematosus, degenerative rheumatic diseases, extra-articular rheumatic and parrarheumatic diseases, for example gout and osteoporosis.

The invention relates especially to compounds of formula I wherein $R_1$ is $C_1-C_4$alkyl, $C_3-C_5$alk-2-en-1-yl or $C_3-C_5$alk-2-yn-1-yl, $R_2$ and $R_3$ independently of one another are hydrogen, or identical $C_1-C_4$alkyl radicals or $C_1-C_4$alkylidene, and $R_4$ is hydrogen, $C_1-C_4$alkyl, $C_1-C_2$alkoxy, phenyl or phenyl-lower alkyl or the group $—C(=O)—R_6$ wherein $R_6$ is $C_1-C_4$alkyl, phenyl, naphthyl, pyridyl, thienyl, pyrryl, furyl, phenoxy, phenyl-$C_1$-$C_4$alkoxy or $C_3-C_5$alk-2-en- 1-yloxy, $R_5$ is phenyl, naphthyl, phenyl-lower alkyl, pyridyl-, thienyl-, pyrryl- or furyl-, pyrrolidinyl-, tetrahydrofuranyl- or tetrahydropyranyl-lower alkyl or $C_1-C_4$alkoxycarbonyl$C_1-C_4$alkyl or the group $—C(=O)—R_7$ wherein $R_7$ has the meaning of $R_6$ as defined for $R_4$ or is phenyl-lower alkyl or phenyl-lower alkenyl, or, when $R_4$ is other than hydrogen, $R_5$ is also $C_1-C_4$alkyl, $C_3-C_5$alk-2-en-1-yl or $C_3-C_$ 5alk-2-yn-1-yl, and to the salts thereof, especially the pharmaceutically acceptable salts thereof.

The invention relates more especially to compounds of formula I wherein $R^1$ is $C_3-C_5$alk-2-en-1-yl, such as allyl or methallyl, or $C_3-C_5$alk-2-yn-1-yl, such as prop-2-yn-1-yl, $R_2$ and $R_3$ are both hydrogen or identical $C_1-C_4$alkyl radicals, such as methyl groups, $R_4$ is hydrogen, $C_1-C_4$alkyl, such as methyl or ethyl, $C_1-C_2$alkoxy, such as methoxy or ethoxy, phenyl, phenyl-lower alkyl, such as benzyl or phenylethyl, or the group $—C(=O)—R_6$ wherein $R_6$ is a $C_1-C_4$alkyl group, such as the methyl group, phenyl, pyridyl, thienyl, phenoxy, benzyloxy or $C_3-C_5$alk-2-en-1-yloxy, such as allyloxy or methallyloxy, and $R_5$ is phenyl, phenyl-lower alkyl, such as benzyl or phenylethyl, pyridyl-, thienyl-, pyrryl-, furyl- or pyrrolidinyl-, tetrahydrofuranyl- or tetrahydropyranyl-lower alkyl, such as pyridyl-, thienyl-, pyrryl- or furyl-, pyrrolidinyl-, tetrahydrofuranyl- or tetrahydropyranyl-methyl, $C_1-C_4$alkoxycarbonyl-$C_1-C_4$alkyl, such as methoxycarbonyl- or ethoxycarbonyl-methyl or -ethyl, or the group $—C(=O)—R_7$ wherein $R_7$ has the meaning of $R_6$ as defined for $R_4$ or is benzyl or phenylallyl, or, when $R_4$ is other than hydrogen, $R_5$ may also be $C_1-C_4$alkyl, such as methyl, $C_3-C_5$alk-2-en-1-yl, such as allyl or methallyl, $C_3-C_5$alk-2-yn-1-yl, such as prop-2-yn-1-yl, and to the salts thereof, especially the pharmaceutically acceptable salts thereof.

The invention relates more especially to compounds of formula I wherein $R^1$ is allyl or methallyl, $R_2$ and $R_3$ are both hydrogen, $R_4$ is hydrogen, methyl or methoxy or the group $—C(=O)—R_6$ wherein $R_6$ is methyl, phenyl, phenoxy, benzyloxy or allyloxy and $R_5$ is phenyl, benzyl, pyridyl-, furyl- or tetrahydrofuranyl-methyl or methoxycarbonylmethyl or the group $—C(=O)—R_7$ wherein $R_7$ has the meaning of $R_6$ as defined for $R_4$ or is benzyl or phenylallyl, or, when $R_4$ is other than hydrogen, $R_5$ is also methyl, allyl, methallyl or prop-2-yn-1-yl, and to the salts thereof, especially the pharmaceutically acceptable salts thereof.

The invention relates specifically to the compounds of formula I mentioned in the Examples and to the salts thereof, especially the pharmaceutically acceptable salts thereof.

Compounds of formula I can be prepared in a manner known per se by reacting a) a compound of formula II

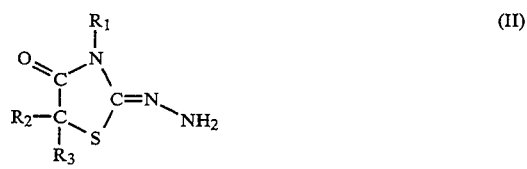

wherein $R_1$, $R_2$ and $R_3$ are as defined above, with an isothiocyanate compound of formula III

R$_5$-NCS    (III).

The condensation of the compounds of formula II with compounds of formula III is effected in customary manner in a protic or aprotic solvent, such as an aliphatic halogenareal hydrocarbon, such as dichloromethane, especially methylene chloride, or an aliphatic or cycloaliphatic ether, for example tetrahydrofuran or dioxane. Further suitable solvents are, for example, acetonitrile, ethanol and toluene.

The compounds are reacted at a temperature of from −50° C. to +120° C., advantageously at from 0° C. to 80° C., where appropriate in the presence of a basic condensation agent, such as dimethylaminopyridine, triethylamine, quinoline or pyridine.

Some of the starting compounds of formula III above wherein $R_5$ is the group —C(=O)—$R_7$ are unstable and, where appropriate, are obtained in the nascent state from corresponding acid halides, especially acid chlorides, of formula IIIa

(IIIa)

wherein $R_7$ is as defined above and X is a halogen atom, especially a chlorine atom, by reaction with a metal isothiocyanate, for example an alkali metal isothiocyanate or ammonium isothiocyanate.

The starting compounds of formula II are known and are described in DE-OS-2 035 419 and in Swiss Patent Specification No. 511 877.

It is generally possible, however, to prepare the isothiocyanate compounds of formula 1II from the corresponding amines of formula IV $R_5$-$NH_2$ (IV), wherein $R_5$ is as defined above, by treatment with thiophosgene.

In accordance with a further process variant b) of process a), it is also possible, however, to prepare compounds of formula I by reacting a compound of formula II with a compound of formula V

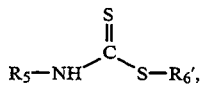

(V)

wherein $R_5$ is as defined above and $R'_6$ is lower alkyl, under condensation conditions analogous to those described above under process variant a).

Compounds of formula V are obtained by reacting the corresponding amines of formula IV, $R_5NH_2$, with carbon disulfide and subsequently treating the product thereof with a lower alkyl halide, especially a lower alkyl iodide.

In accordance with a further process c), compounds of formula I can be prepared by reacting a compound of formula VI

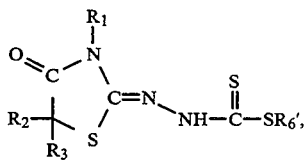

(VI)

wherein $R_1$, $R_2$ and $R_3$ are as defined above and $R'_6$ is a lower alkyl radical, with a corresponding amine of formula IV above $R_5$-$NH_2$ (IV), wherein $R_5$ is as defined above.

The condensation of the compounds of formula VI with compounds of formula IV is effected in customary manner, advantageously in a protic or aprotic solvent, such as an aliphatic halogenated hydrocarbon, such as dichloromethane, especially methylene chloride, or an aliphatic or cycloaliphatic ether, for example tetrahydrofuran or dioxane. Further suitable solvents are, for example, acetonitrile, ethanol and toluene.

The compounds are reacted at a temperature of from 25° C. to 120° C., advantageously at the boiling temperature of the solvent, in the presence of a basic condensation agent, such as dimethylaminopyridine, a tri-lower alkylamine, for example triethylamine, or quinoline or pyridine.

Starting compounds of formula VI are novel and can be obtained from the corresponding above-mentioned hydrazone compound of formula II

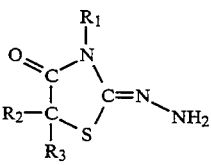

(II)

by reaction with carbon disulfide, $CS_2$, and subsequent macdon with a lower alkyl iodide. The reaction of a compound of formula II with carbon disulfide is carried out in the presence of a tertiary organic base, such as a tri-lower alkylamine, a Hünig base or an organic nitrogen base, such as pyridinc or quinolinc. The subsequent reaction with a lower alkyl iodide is carried out with cooling of the resulting reaction mixture to a temperature of from −10° C. to +10° C., preferably at a temperature of from 0° C. to +5° C.

In accordance with a further process d), compounds of formula I wherein $R_4$ is lower alkyl, lower alkoxy, aryl or aryl-lower alkyl can be prepared by ting-closing compounds of formula VII

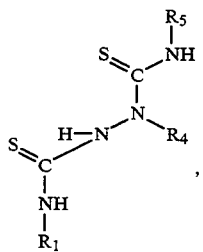

(VII)

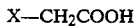

wherein $R_4$ is as defined above and $R_5$ is as defined for formula I, with a haloacetic acid of formula VIII

X—$CH_2COOH$ (VIII), wherein X is a halogen atom, especially a bromine atom, to form the corresponding thiazolidinone-thiosemicarbazone of formula I.

The reaction is carried out in the presence of a basic condensation agent, such as sodium acetate, at a temperature of from 25° C. to 80° C., preferably at a temperature of from 30° C. to 50° C.

The condensation of the compounds of formula VH with compounds of formula VIH is effected in customary manner in a protic or aprotic solvent, such as an aliphatic or cycloaliphatic ether, for example tetrahydrofuran or dioxane, but preferably ethanol or acetonitrile.

Compounds of formula VII can be obtained from the corresponding thiosemicarbazide of formula IX

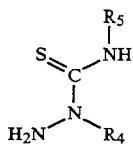
(IX)

by reaction with an isothiocyanate of formula X

R₁-NCS    (X).

The condensation of the compounds of formula IX with compounds of formula X is effected in customary manner in a protic or aprotic solvent, such as an aliphatic halogenated hydrocarbon, such as dichloromethane, especially methylene chloride, or an aliphatic or cycloaliphatic ether, for example tetrahydrofuran or dioxane. Examples of further suitable solvents are acetonitrile, ethanol and toluene.

The compounds are reacted at a temperature of from 25° C. to 120° C., advantageously at the boiling temperature of the solvent, in the presence of a basic condensation agent, such as dimethylaminopyridine, triethylamine or pyridine.

Compounds of formula IX can be obtained from the corresponding hydrazines of formula XI

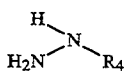
(XI)

by reaction with an isothiocyanate of formula III

R₅-NCS    (III).

The condensation of the compounds of formula XI with compounds of formula XII is effected in customary manner in a protic or aprotic solvent, such as an aliphatic halogenated hydrocarbon, such as dichloromethane, especially methylene chloride, or an aliphatic or cycloaliphatic ether, for example tetrahydrofuran or dioxane. Further suitable solvents are, for example, acetonitrite, ethanol and toluene.

The compounds are reacted with one another at a temperature of from −10° C. to +30° C., preferably from 0° C. to +20° C.

Compounds of formula I obtainable in accordance with the invention by process variants a)–d) that are in the form of a mixture of isomers can, if desired, be separated into the individual isomers and/or free compounds obtainable in accordance with the invention can be converted into a salt or a salt obtainable in accordance with the invention can be converted into a free compound or into a different salt.

Compounds obtainable in accordance with the process can be converted in customary manner into different compounds of formula I.

For example, compounds of formula I

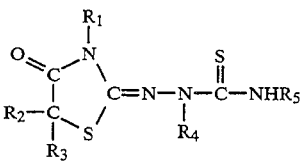

wherein R₁, R₂, R₃ and R₅ are as defined above and R₄ is hydrogen can be reacted with an acid halide of formula IIIb, X—C(=O)—R₆ wherein X is a halogen atom, to form compounds of formula I wherein R₄ is the group

Resulting salts can be convened into the free compounds in a manner known per se, for example by treatment with a base, such as an alkali metal hydroxide, a metal carbonate or a metal hydrogen carbonate, or with ammonia, or another salt-forming base mentioned at the beginning, or with an acid, such as a mineral acid, for example with hydrochloric acid, or another salt-forming acid mentioned at the beginning.

Resulting salts can be convened into different salts in a manner known per se, acid addition salts for example by treatment with a suitable metal salt, such as a sodium, barium or silver salt, of a different acid in a suitable solvent in which an inorganic salt being formed is insoluble and is therefore eliminated from the reaction equilibrium, and base salts by freeing the free acid and convening it into a salt again.

The compounds of formula I, including their salts, may also be obtained in the form of hydrates or may include the solvent used for crystallisation.

In view of the close relationship between the novel compounds in free form and in the form of their salts, hereinbefore and hereinafter any reference to the free compounds or their salts should be understood as including the corresponding salts or free compounds, respectively, as appropriate and expedient.

Resulting racemates can also be resolved into the optical antipodes by known methods, for example by recrystallisation from an optically active solvent, with the aid of microorganisms or by reaction of the resulting diastereoisomeric mixture or racemate with an optically active auxiliary compound, for example according to the acidic, basic or functionally modifiable groups contained in compounds of formula I, with an optically active acid, base or an optically active alcohol, to form mixtures of diastereoisomeric salts or functional derivatives, such as esters, and separation of the same into the dimstereoisomers from which the desired enantiomer can be freed in customary manner. Bases, acids and alcohols suitable for the purpose are, for example, optically active alkaloid bases, such as strychnine, cinchonine or brucine, or D- or L-( 1-phenyl)ethylamine, 3-pipecoline, ephedrine, amphetamine and similar bases that can be obtained by synthesis, optically active carboxylic or sulfonic acids, such as quinic acid or D- or L-tartaric acid, D- or L-di-o-toluoyltartafic acid, D- or L-malic acid, D- or L-mandelic acid, or D- or L-camphorsulfonic acid, or Optically active alcohols, such as borneol or D- or L-( 1-phenyl)ethanol.

The invention relates also to those forms of the process according to which a compound obtainable as intermediate at any stage of the process is used as starting material and the remaining steps are carried out, or a starting material is used in the form of a salt or, especially, is formed under the reaction conditions.

The invention relates also to the novel starting materials which have been developed specifically for the preparation of the compounds according to the invention, especially the group of starting materials that lead to the compounds of formula I mentioned at the beginning as being preferred, to the processes for their preparation and to their use as intermediates.

The pharmaceutical compositions according to the invention, which comprise the compound according to the invention or pharmaceutically acceptable salts thereof, are for enteral, such as oral, and also rectal, and parenteral administration to (a) warm-blooded animal(s), and comprise the pharmacological active ingredient on its own or together with a pharmaceutically acceptable carrier. The daily dose of active ingredient is dependent on the age and individual condition as well as on the mode of administration.

The novel pharmaceutical compositions comprise, for example, from about 10% to about 80%, preferably from about 20% to about 60%, active ingredient. Pharmaceutical compositions according to the invention for enteral and/or parenteral administration are, for example, those in unit dose form, such as dragées, tablets, capsules or suppositories, as well as ampoules. They can be prepared in a manner known per se, for example by means of conventional mixing, granulating, confectioning, dissolving or lyophilising processes. For example, pharmaceutical compositions for oral administration can be obtained by combining the active ingredient with solid carders, optionally granulating a resulting mixture, and, if desired, processing the mixture or granules, if necessary with the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using, for example, corn, wheat, rice or potato starch, gelatin, tragacanth, methylcellulose and/or polyvinylpyrrolidone, if desired, disintegrators, such as the above-mentioned starches, also carboxymethyl starch, cross-linked polyvinylpyrrolidone, agar, alginic acid or a salt thereof, such as sodium alginate. Excipients are especially flow agents, flow conditioners and lubricants, for example silicic acid, talc, stearic acid or salts thereof, such as magnesium or calcium stearate, and/or polyethylene glycol. Dragée cores are provided with suitable, optionally enteric, coatings, there being used inter alia concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Colourings or pigments may be added to the tablets or drag6e coatings, for example for identification purposes or to indicate different doses of active ingredient.

Other orally administrable pharmaceutical compositions are dry-filled capsules comprising gelatin, and also soft sealed capsules comprising gelatin and a plasticiser, such as glycerol or sorbitol. The dry-filled capsules may comprise the active ingredient in the form of granules, for example in admixture with fillers, such as lactose, binders, such as starches, and/or glidants, such as talc or magnesium stearate, and, if desired, stabilisers. In soft capsules, the active ingredient is preferably dissolved or suspended in suitable liquids, such as fatty oils, paraffin oil or liquid polyethylene glycol, to which stabilisers may also have been added.

Suitable rectally administrable pharmaceutical compositions are, for example, suppositories that comprise a combination of the active ingredient with a suppository base. Suitable suppository bases are, for example, natural or synthetic triglycerides, paraffin hydrocarbons, polyethylene glycol or higher alkanols. There may also be used gelatin rectal capsules, which comprise a combination of the active ingredient with a base material. Suitable base materials are, for example, liquid triglycerides, polyethylene glycol or paraffin hydrocarbons.

Suitable for parenteral administration are especially aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that comprise viscosity-increasing substances, for example sodium carboxymethylcellulose, sorbitol and/or dextran, and, optionally, stabilisers.

The invention relates also to the use of the compounds of formula I, preferably in the form of pharmaceutical compositions. The dose of active ingredient is dependent on the species of warm-blooded animal, the age and the individual condition, as well as on the mode of administration. In normal cases, the approximate daily dose in the case of oral administration to a patient weighing about 75 kg is estimated to be from about 5 mg to about 1000 mg, especially from about 10 mg to about 200 mg. The dose can be administered all at once or may be divided into several, for example from 2 to 4, individual doses. Pharmaceutical compositions in unit dose form thus comprise from about 5 mg to about 250 mg, especially from about 10 mg to about 50 mg, of active ingredient.

The Examples that follow serve to illustrate the invention; temperatures are given in degrees Celsius, pressures in mbar.

EXAMPLE 1:

1.0 g of 1-(3-allyl-4-oxo-thiazolidin-2-ylidene)-hydrazone and 0.87 g of phenyl isothiocyanate are stirred for 1 hour at room temperature in 15 ml of ethanol as solvent. The product, which crystallises readily, is filtered off, washed with cold ethanol or ether and petroleum ether and dried under a high vacuum to yield crystalline 1-(3-allyl-4-oxo-thiazolidin-2-ylidene)-4-phenyl-thiosemicarbazone, m.p. 156°–158° C.

EXAMPLE 2:

Analogously to Example 1, 1 g of 1-(3-allyl-4-oxo-thiazolidin-2-ylidene)hydrazone and 1.38 g of p-bromophenyl isothiocyanate in 15 ml of ethanol are heated for 0.5 hour at 50° C. After filtration, there are obtained analogously to the manner described in Example 1 crystals of 1-(3-allyl-4-oxo-thiazolidin-2-ylidene)-4-p-bromophenyl-thiosemicarbazone, m.p. 178°–180° C.

EXAMPLE 3:

Analogously to Example 1, 0.7 g of 1-(3-allyl-4-oxo-thiazolidin-2-ylidene)hydrazone and 0.7 g of p-fluorophenyl isothiocyanate in 15 ml of ethanol are boiled under reflux for 1 hour. Filtration yields crystals of 1-(3-allyl-4-oxo-thiazolidin-2-ylidene)-4-p-fluorophenyl-thiosemicarbazone, m.p. 152°–154° C.

EXAMPLE 4:

0.65 g of 1-(3-allyl-4-oxo-thiazolidin-2-ylidene)-hydrazono-1-dithioformic acid methyl ester amide and 0.27 g of 4-aminophenol are heated under reflux for 5 hours with a catalytic amount of dimethylaminopyridine in 20 ml of ethanol until the reaction is complete. After cooling, the resulting crystallising product, 1-(3-allyl-4-oxo-thiazolidin-2-ylidene)-4-p-hydroxyphenyl-thiosemicarbazone, is filtered off, m.p. 212°–214° C.

EXAMPLE 5:

Analogously to Example 1, 0.7 g of 1-(3-allyl-4-oxo-thiazolidin-2-ylidene)hydrazone and 0.6 ml of pentafluorophenyl isothiocyanate in 15 ml of ethanol are boiled under reflux for 1 hour. After cooling crystals of the resulting 1-(3-allyl-4-oxo-thiazolidin-2-ylidene)-4-pentafluorophenyl-thiosemicarbazone are filtered off, m.p. 176°–178° C.

EXAMPLE 6:

Analogously to Example 1, 1 g of 1-(3-allyl-4-oxo-thiazolidin-2-ylidene)hydrazone and 1 g of tolyl isothiocyanate in 20 ml of ethanol are boiled under reflux for 1 hour. After filtration, crystals of 1-(3-allyl-4-oxo-thiazolidin-2-ylidene)-4-tolyl-thiosemicarbazone are obtained, m.p 173°–175° C.

EXAMPLE 7:

Analogously to Example 4, 0.75 g of 1-(3-allyl-4-oxo-thiazolidin-2-ylidene) hydrazono-1-dithioformic acid methyl ester amide and 0.4 g of 4-aminobenzonitrile are boiled under reflux for 5 hours with a catalytic amount of dimethylaminopyridine in 20 ml of ethanol. After filtration, crystals of 1-(3-allyl-4-oxo-thiazolidin-2-ylidene)-4-p-cyanophenyl-thiosemicarbazone are obtained, m.p. 192°–193° C.

EXAMPLE 8:

Analogously to Example 1, 2 g of 1-(3-allyl-4-oxo-thiazolidin-2-ylidene)hydrazone and 1.75 g of benzyl isothiocyanate in 30 ml of ethanol are boiled under reflux for 2 hours. After filtration, crystals of 1-(3-allyl-4-oxo-thiazolidin-2-ylidene)-4-benzylthiosemicarbazone are obtained, m.p. 120° C.

EXAMPLE 9:

Analogously to Example 1, 1 g of 1-(3-allyl-4-oxo-thiazolidin-2-ylidene)hydrazone and 1.35 g of thiophene-2-methyl isothiocyanate in 20 ml of ethanol are boiled under reflux for 0.5 hour. After filtration, crystals of 1-(3-allyl-4-oxo-thiazolidin-2-ylidene)-4-(thiophene-2-methyl)-thiosemicarbazone are obtained, m.p. 114°–115° C.

EXAMPLE 10:

Analogously to Example 1, 0.5 g of 1-(3-allyl-4-oxo-thiazolidin-2-ylidene)hydrazone and 1.0 g of furan-2-methyl isothiocyanate in 20 ml of ethanol are boiled under reflux for 0.5 hour. After filtration, crystals of 1-(3-allyl-4-oxo-thiazolidin-2-ylidene)-4-(furan-2-methyl)-thiosemicarbazone are obtained, m.p. 120°–122° C.

EXAMPLE 11:

Analogously to Example 1, 1.6 g of 1-(3-allyl-4-oxo-thiazolidin-2-ylidene)hydrazone and 1.4 g of tetrahydrofuran-2-methyl isothiocyanate in 20 ml of ethanol are boiled under reflux for 1 hour. After filtration and recrystallisation twice from ethanol/methylene chloride, crystals of 1-(3-allyl-4-oxo-thiazolidin-2-ylidene)-4-(tetrahydrofuran-2-methyl)-thiosemicarbazone are obtained, m.p. 120°–122° C.

EXAMPLE 12:

Analogously to Example 4, 0.7 g of 2-(3-allyl-4-oxo-thiazolidin-2-ylidene) hydrazono-1-dithioformic acid methyl ester amide and 0.32 g of 2-picolylamine in 20 ml of ethanol are boiled under reflux for 3 hours with a catalytic amount of dimethylaminopyfidine. Mter filtration, crystals of 1-(3-allyl-4-oxo-thiazolidin-2-ylidene)-4-(2-picolyl)-thiosemicarbazone are obtained, m.p. 177°–178° C.

EXAMPLE 13:

Analogously to Example 1, 1 g of 1-(3-ally14-oxo-thiazolidin-2-ylidene)hydrazone and 1.1 g of phenylethyl isothiocyanate in 20 ml of ethanol axe heated for 1 hour at 50° C. After cooling and filtration, crystals of 1-(3-allyl-4-oxo-thiazolidin-2-ylidene)-4-phenylethyl-thiosemicarbazone are obtained, m.p. 140°–141 ° C.

EXAMPLE 14:

Analogously to Example 1, 1.7 g of 1-(3-allyl-4-oxo-thiazolidin-2-ylidene)hydrazone and 1.4 g of glycine ethyl ester isocyanate in 25 ml of ethanol are boiled under reflux for 1.5 hours. The mixture is cooled and then concentrated. The crude product is recrystallised from methylene chloride/ether/petroleum ether to yield 1-(3-allyl-4-oxothiazolidin-2-ylidene)-4-glycinyl ethyl ester thiosemicarbazone, m.p. 131°–132° C.

EXAMPLE 15:

Analogously to Example 1, 5 g of 1-(5,5-dimethyl-3-methallyl-4-oxo-thiazolidin-2-ylidene)-hydrazone and 3.2 g of glycine ethyl ester isothiocyanate in 80 ml of ethanol are boiled under reflux for 3 hours. After cooling and filtration, the resulting crude product is chromatographed on silica gel with methylene chloride and recrystallised from ether/petroleum ether to yield 1-(5,5-dimethyl-3-methallyl-4-oxo-thiazolidin-2-ylidene)-4-glycinyl ethyl ester thiosemicarbazone, m.p. 112°–113° C.

EXAMPLE 16:

Analogously to Example 4, 0.65 g of 2-(3-allyl-4-oxo-thiazolidin-2-ylidene)-hydrazono-1-dithioformic acid methyl ester amide and 0.3 ml of aminoacetaldehyde-dimethylacetal in 20 ml of ethanol are boiled under reflux for 12 hours with a catalytic amount of dimethylaminopyridine. The solvent is removed and crystals of 1-(3-allyl-4-oxo-thiazolidin-2-ylidene)-4-(2',2'-dimethoxyethyl)-thiosemicarbazone are obtained from methylene chloride/ether; m.p. 113°–114° C.

EXAMPLE 17:

1.9 g of 4-allyl-1-methyl-thiosemicarbazone-1-methylamino-thioamide are mixed with 1.5 g of bromoacetic acid and 1.75 g of anhydrous sodium acetate in 20 ml of ethanol as solvent and the reaction mixture is stirred for 6 hours at room temperature and then for a further 14 hours at 50° C. After cooling, the solvent is removed using a rotary evaporator and the resulting crude product is chromatographed on silica gel with methylene chloride and then recrystallised from methylene chloride/ether to yield crystalline 1-(3-allyl-4-oxo-thiazolidin-2-ylidene )-2,4-dimethyl-thiosemicarbazone, m.p. 142°–143° C.

EXAMPLE 18:

Analogously to Example 4, 1.3 g of 2-(3-allyl-4-oxo-thiazolidin-2-ylidene)hydrazono-1-dithioformic acid methyl ester amide and 0.7 g of 2-aminobenzyl alcohol in 20 ml of ethanol are boiled under reflux for 8 hours with a catalytic amount of dimethylaminopyridine. After removal of the solvent, crystals of 1-(3-allyl-4-oxo-thiazolidin-2-ylidene)-4-hydroxymethylphenyl-thiosemicarbazone are obtained from methylene chloride/ether, m.p. 146°–147° C.

EXAMPLE 19:

Analogously to Example 4, 1.0 g of 2-(3-allyl-4-oxo-thiazolidin-2-ylidene)hydrazono-1-dithioformic acid methyl ester amide and 0.58 g of 3,4-methylenedioxyaniline in 20 ml of ethanol are boiled under reflux for 7 hours with a catalytic amount of dimethylaminopyridine. After removal of the solvent, crystals of 1-(3-allyl-4-oxo-thiazolidin-2-ylidene)-4-(3,4-methylenedioxyphen-1-yl)-thiosemicarbazone are obtained from methylene chloride/ether, m.p. 165°–167° C.

EXAMPLE 20:

Analogously to Example 4, 3.5 g of 2-(3-allyl-4-oxo-thiazolidin-2-ylidene)hydrazono-1-dithioformic acid methyl ester amide and 2.1 g of D,L-alanine methyl ester hydrochloride in 20 ml of ethanol and 2.1 ml of triethylamine are boiled under reflux for 8 hours with a catalytic amount of dimethylaminopyridine. After cooling, the solvent is removed using a rotary evaporator and the resulting crude product is chromatographed on silica gel with methylene chloride/acetone and then recrystallised from methylene chloride/ether to yield crystalline 1-(3-allyl-4-oxo-thiazolidin-2-ylidene)-4-(propionic acid ethyl ester-2-yl)-thiosemicarbazone, m.p. 110°–111 ° C.

EXAMPLE 21:

With stirring at 0° C., 1.4 ml of isobutyric acid chloride are added dropwise to a suspensidn of 1.35 g of potassium rhodanide in 30 ml of acetonitrile and the temperature of the reaction mixture-is allowed to rise to room temperature. After 30 minutes, 2 g of 1-(3-allyl-4-oxo-thiazolidin-2-ylidene)-hydrazone are added dropwise thereto and the resulting mixture is stirred for 3 hours at room temperature until the reaction is complete. The solvent is removed using a rotary evaporator and the resulting residue is taken up in methylene chloride, washed with water, dried over magnesium sulfate and concentrated to ⅔ of its volume. After the addition of ether, the resulting product crystallises out and after being ffitered off is recrystallised from methylene chloride/ether to yield pure crystals of 1-(3-allyl-4-oxo-thiazolidin-2-ylidene)-4-(2-methyl-propionyl)-thiosemicarbazone, m.p. 165°–166 ° C.

EXAMPLE 22:

1.2 g of benzoyl isothiocyanate are introduced into 30 ml of acetonitrile, and 2 g of 1-(5,5-dimethyl-3-methallyl-4-oxo-thiazolidin-2-ylidene)-hydrazone in a small amount of acetonitrile are added dropwise thereto. The mixture is heated under reflux with stirring for 1.5 hours and then cooled to room temperature. The solid material is filtered off and washed with ether/petroleum ether and the resulting crude product is chromatographed on silica gel with methylene chloride to yield 1-(5,5-dimethyl-3-methallyl-4-oxo-thiazolidin-2-ylidene)-4-benzoyl-thiosemicarbazone, m.p. 152°–155 ° C.

EXAMPLE 23:

Analogously to Example 21, 1.4 ml of thiophene-2-carboxylic acid chloride are added at 0° C. to 1.35 g of potassium rhodanide in 30 ml of acetonitrile and then 2 g of 1-(3-allyl-4-oxo-thiazolidin-2-ylidene)-hydrazone are added thereto. The mixture is then stirred for 3.5 hours at room temperature. Working up and subsequent recrystallisation from methylene chloride/ether yield crystals of 1-(3-allyl-4-oxo-thiazolidin-2-ylidene)-4-(thiophene-2-carbonyl)-thiosemicarbazone, m.p. 185° C.

EXAMPLE 24:

Analogously to Example 21, 1.73 ml of phenylacetyl chloride are added at 0° C. to 1.35 e.g. of potassium rhodanide in 30 ml of acetonitrile and then 2.0 g of 1-(3-allyl-4-oxo-thiazolidin-2-ylidene)-hydrazone are added thereto. The mixture is then stirred for 3 hours at room temperature. Working up and subsequent recrystallisation from methylene chloride/ether yield crystals of 1-(3-allyl-4-oxo-thiazolidin-2-ylidene)-4-phenylacetyl-thiosemicarbazone, m.p. 190°–191 ° C.

EXAMPLE 25:

Analogously to Example 21, 1.4 ml of chloroformic acid phenyl ester are added at 0° C. to 0.85 g of ammonium rhodanide in 30 ml of acetonitrile and then 1.7 g of 1-(3-allyl-4-oxo-thiazolidin-2-ylidene)-hydrazone are added thereto. The mixture is then stirred for 15 minutes at room temperature. Working up and subsequent recrystallisation from ethanol/methylene chloride yield crystals of 1-(3-allyl-4-oxo-thiazolidin-2-ylidene)-4-phenoxycarbonyl-thiosemicarbazone, m.p. 173 ° C. (decomposition).

EXAMPLE 26:

Analogously to Example 21, 0.9 ml of chloroformic acid benzyl ester are added at 0° C. to 0.7 g of potassium rhodanide in 30 ml of acetonitrile and then 1 g of 1-(3-allyl-4-oxo-thiazolidin-2-ylidene)-hydrazone is added thereto. The mixture is then stirred for 3 hours at room temperature. Working up and subsequent recrystallisation from ethanol/methylene chloride yield crystals of 1-(3-allyl-4-oxo-thiazolidin-2-ylidene)-4-benzyloxycarbonyl-thiosemicarbazone, m.p. 165° C.

EXAMPLE 27:

With stirring at 0° C., 0.8 ml of acetyl chloride is added to a mixture of 2.4 g of 1-(3-allyl-4-oxo-thiazolidin-2-ylidene)-4-methyl-thiosemicarbazone and 1.5 ml of triethylamine in 20 ml of methylene chloride and the reaction mixture is then allowed to warm to room temperature. After stirring for 1 hour at room temperature the mixture is extracted with water and the organic phase is dried over magnesium sulfate and concentrated. The crude product is recrystallised from ether/methylene chloride and the product that has been filtered off is dried under a high vacuum to yield crystals of 1-(3-allyl-4-oxo-thiazolidin-2-ylidene)-2-acetyl-4-methyl-thiosemicarbazone, m.p. 125° C.

EXAMPLE 28:

Analogously to Example 27, with stirring at 0° C. 1.3 ml of benzoyl chloride are added to 2 g of 1-(3-allyl-4-oxo-thiazolidin-2-ylidene)-4-thiosemicarbazone and 1.5 ml of triethylamine in 20 ml of methylene chloride. Working up and subsequent crystallisation from ether yield crystals of 1-(3-allyl-4-oxo-thiazolidin-2-ylidene)-2-benzoyl-4-methyl-thiosemicarbazone, m.p. 113 ° C.

EXAMPLE 29:

Analogously to Example 21, 1.2 ml of chloroformic acid allyl ester are added at 0° C. to 1.0 g of potassium rhodanide in 30 ml of acetonitrile and then 1.2 g of 1-(3-allyl-4-oxo-thiazolidin-2-ylidene)-hydrazone are added thereto. The mixture is then stirred for 3 hours at room temperature. Working up and subsequent recrystallisation from ethanol/methylene chloride yield crystals of 1-(3-allyl-4-oxo-thiazolidin-2-ylidene)-4-allyloxycarbonyl-thiosemicarbazone.

EXAMPLE 30:

Analogously to Example 21, 1.82 g of cinnamic acid chloride are added at 0° C. to 0.85 g of ammonium rhodanide in 30 ml of acetonitrile and then 1.7 g of 1-(3-allyl-4-oxo-thiazolidin-2-ylidene)-hydrazone are added thereto. The resulting mixture is then stirred for 3 hours at room temperature. After working up and subsequent recrystallisation from methylene chloride/ether, first acylated hydrazone is separated off as secondary product and then there are obtained from the mother liquor, after the addition of a further portion of ether, crystals of 1-(3-allyl-4-oxo-thiazolidin-2-ylidene)-4-cinnamoyl-thiosemicarbazone, m.p. 142°–144° C.

EXAMPLE 31:

Tablets, each comprising 10 mg of active ingredient, can be prepared as follows:

| Composition (10000 tablets) | |
|---|---|
| active ingredient | 100.0 g |
| lactose | 450.0 g |
| potoato starch | 350.0 g |
| gelatin | 10.0 g |
| talcum | 60.0 g |
| magnesium stearate | 10.0 g |
| silicon dioxide (highly dispersed) | 20.0 g |
| ethanol | q.s. |

The active ingredient is mixed with the lactose and 292 g of the potato starch, and the mixture is moistened with an ethanolic solution of the gelatin and granulated through a sieve. After drying, the remainder of the potato starch, the magnesium stearate, the talcum and the silicon dioxide are mixed in and the mixture is compressed to form tablets, each weighing 100.0 mg and comprising 10.0 mg of active ingredient; if desired the tablets may be provided with dividing notches for finer adaptation of the dose.

EXAMPLE 32:

Hard gelatin capsules comprising 20 mg of active ingredient can be prepared, for example, as follows:

| Composition (for 1000 capsules) | |
|---|---|
| active ingredient | 20.0 g |
| lactose | 240.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve of 0.2 mm mesh size. The two components are intimately mixed. Then first the lactose is added through a sieve of 0.6 mm mesh size and then the microcrystalline cellulose is added through a sieve of 0.9 mm mesh size. The mixture is then intimately mixed again for 10 minutes. Finally the magnesium stearate is added through a sieve of 0.8 mm mesh size. After mixing for a further 3 minutes, size 0 hard gelatin capsules are each filled with 300 mg of the resulting formulation.

EXAMPLE 33:

Hard gelatin capsules comprising 100 mg of active ingredient can be prepared, for example, as follows:

| Composition (for 1000 capsules) | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve of 0.2 mm mesh size. The two components are intimately mixed. Then first the lactose is added through a sieve of 0.6 mm mesh size and then the microcrystalline cellulose is added through a sieve of 0.9 mm mesh size. The mixture is then intimately mixed again for 10 minutes. Finally the magnesium stearate is added through a Sieve of 0.8 mm mesh size. After mixing for a further 3 minutes, size 0 hard gelatin capsules are each filled with 390 mg of the resulting formulation.

EXAMPLE 34:

Film-coated tablets each comprising 50 mg of active ingredient can be prepared, for example, as follows:

| Composition (for 100 film-coated tablets) | |
|---|---|
| active ingredient | 50.0 g |
| lactose | 100.0 g |
| corn starch | 70.0 g |
| talcum | 10.0 g |
| calcium stearate | 2.0 g |
| hydroxypropylmethylcellulose | 2.36 g |
| shellac | 0.64 g |
| water | q.s. g |
| methylene chloride | q.s. |

The active ingredient, the lactose and 40 g of the corn starch are mixed and moistened with a paste prepared from 15 g of corn starch and water (with heating) and granulated. The granules are dried, the remainder of the corn starch, the talcum and the calcium stearate are added and mixed with the granules. The mixture is compressed to form tablets (weight: 240 mg) which are then film-coated with a solution of the hydroxypropylmethylcellulose and the shellac in methylene chloride; final weight of the film-coated tablet: 283 mg.

EXAMPLE 35:

A 0.2% injection or infusion solution of an active ingredient can be prepared, for example, as follows:

| Composition for (1000 ampoules) | |
| --- | --- |
| active ingredient | 5.0 g |
| sodium chloride | 22.5 g |
| phosphate buffer pH = 7.4 | 300.0 g |
| demineralised water | ad 2500.0 ml |

The active ingredient and the sodium chloride are dissolved in 1000 ml of water and filtered through a micro filter. The buffer solution is added and the solution is made up to 2500 ml with water. For the preparation of unit dose forms, 1.0 ml or 2.5 ml portions are introduced into glass ampoules, which then each comprise 2.0 mg or 5.0 mg of active ingredient, respectively.

EXAMPLE 36:

A 1% ointment (o/w emulsion), comprising an active ingredient, having the following composition:

| active ingredient | 1.0 g |
| --- | --- |
| cetyl alcohol | 3.0 g |
| glycerol | 6.0 g |
| methylparaben | 0.18 g |
| propylparaben | 0.05 g |
| Arlacel 60 | 0.6 g |
| Tween 60 | 4.4 g |
| stearic acid | 9.0 g |
| isopropyl palmitate | 2.0 g |
| paraffin oil, viscous | 10.0 g |
| demin. water, q.s. ad | 100.0 g |

EXAMPLE 37:

A 1% gel, comprising an active ingredient, having the following composition:

| active ingredient | 1.0 g |
| --- | --- |
| Carbopol 934 P | 1.0 g |
| glycerol | 3.0 g |
| isopropanol | 25.0 g |
| Softigen ®767 | 0.2 g |
| demin. water, q.s. ad | 100.0 g |

What is claimed is:
1. A compound of formula I

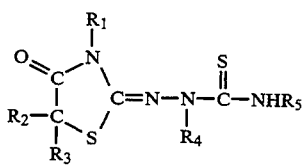

wherein
$R_1$ is lower alkyl, lower alk-2-en-1-yl or lower alk-2-yn-1-yl,
$R_2$ and $R_3$ independently of one another are hydrogen or lower alkyl, or $R_2$ and $R_3$ together are lower alkylidene,
$R_4$ is hydrogen, lower alkyl, lower alkoxy, aryl, aryl-lower alkyl or the group —C(=O)—$R_6$ wherein $R_6$ is lower alkyl, aryl, heteroaryl, aryloxy, aryl-lower alkoxy or lower alk-2-en-1-yloxy,
$R_5$ is aryl, aryl-lower alkyl, unsaturated or saturated heterocyclyl-lower alkyl, lower alkoxycarbonyl-lower alkyl or the group —C(=O)—$R_7$ wherein $R_7$ is lower alkyl, aryl, aryl-lower alkyl, aryl-lower alkenyl, heteroaryl, aryloxy, aryl-lower alkoxy or lower alk-2-en-1-yloxy, or a salt thereof.

2. A compound according to claim 1 of formula I, wherein
$R_1$ is $C_1$–$C_4$alkyl, $C_3$–$C_5$alk-2-en-1-yl or $C_3$–$C_5$alk-2-yn-1-yl,
$R_2$ and $R_3$ independently of one another are hydrogen, or identical $C_1$–$C_4$alkyl radicals or $C_1$–$C_4$alkylidene, and
$R_4$ is hydrogen, $C_1$–$C_4$alkyl, $C_1$–$C_2$alkoxy, phenyl or phenyl-lower alkyl or the group —C(=O)—$R_6$ wherein $R_6$ is $C_1$–$C_4$alkyl, phenyl, naphthyl, pyridyl, thienyl, pyrryl, furyl, phenoxy, phenyl-$C_1$–$C_4$alkoxy or $C_3$–$C_5$alk-2-en-1-yloxy,
$R_5$ is phenyl, naphthyl, phenyl-lower alkyl, pyridyl-, thienyl-, pyrryl- or furyl-, pyrrolidinyl-, tetrahydrofuranyl- or tetrahydropyranyl-lower alkyl or $C_1$–$C_4$alkoxycarbonyl$C_1$–$C_4$alkyl or the group —C(=O)—$R_7$ wherein $R_7$ has the meaning of $R_6$ as defined for $R_4$ or is phenyl-lower alkyl or phenyl-lower alkenyl, or a pharmaceutically acceptable salt thereof.

3. A compound according to claim 1 of formula I, wherein
$R_1$ is $C_3$–$C_5$alk-2-en-1-yl, such as allyl or methallyl, or $C_3$–$C_5$alk-2-yn-1-yl, such as prop-2-yn-1-yl,
$R_2$ and $R_3$ are both hydrogen or identical $C_1$–$C_4$alkyl radicals, such as methyl groups,
$R_4$ is hydrogen, $C_1$–$C_4$alkyl, such as methyl or ethyl, $C_1$–$C_2$alkoxy, such as methoxy or ethoxy, phenyl, phenyl-lower alkyl, such as benzyl or phenylethyl, or the group —C(=O)—$R_6$ wherein $R_6$ is a $C_1$–$C_4$alkyl group, such as the methyl group, phenyl, pyridyl, thienyl, phenoxy, benzyloxy or $C_3$–$C_5$alk-2-en-1-yloxy, such as allyloxy or methallyloxy, and
$R_5$ is phenyl, phenyl-lower alkyl, such as benzyl, or phenylethyl, pyridyl-, thienyl-, pyrryl-, furyl-, pyrrolidinyl-, tetrahydrofuranyl, or tetrahydropyranyl-lower alkyl, such as pyridyl-, thienyl-, pyrrol- or furyl-, pyrrolidinyl-, tetrahydrofuranyl- or tetrahydrofuranyl-methyl or methoxycarbonylmethyl or -ethyl, or the group —C(=O)—$R_7$ wherein $R_7$ has the meaning of $R_6$ as defined for $R_4$ or is benzyl or phenylallyl, or a pharmaceutically acceptable salt thereof.

4. A compound according to claim 1 of formula I, wherein
$R_1$ is allyl or methallyl,
$R_2$ and $R_3$ are both hydrogen,
$R_4$ is hydrogen, methyl or methoxy or the group —C(=O)—$R_6$ wherein $R^6$ is methyl, phenyl, phenoxy, benzyloxy or allyloxy and
$R_5$ is phenyl, benzyl, pyridyl-, furyl- or tetrahydropyranyl-methyl or methoxycarbonylmethyl or the group —C(=O)—$R_7$ wherein $R_7$ has the meaning of $R_6$ as defined for $R_4$ or is benzyl or phenylallyl, or a pharmaceutically acceptable salt thereof.

5. A compound selected from the group consisting of 1-(3-Allyl-4-oxo-thiazolidin-2-ylidene)-4-phenyl-thiosemicarbazone,
1-(3-Allyl-4-oxo-thiazolidin-2-ylidene)-4-p-bromophenyl-thiosemicarbazone, 1-(3-Allyl-4-oxo-thiazolidin-2-ylidene)-4-p-fluorophenyl-thiosemicarbazone,
1-(3-Allyl-4-oxo-thiazolidin-2-ylidene)-4-pentafluorophenyl-thiosemicarbazone,
1-(3-Allyl-4-oxo-thiazolidin-2-ylidene)-4-tolyl-thiosemicarbazone,
1-(3-Allyl-4-oxo-thiazolidin-2-ylidene)-4-p-cyanophenyl-thiosemicarbazone,
1-(3-Allyl-4-oxo-thiazolidin-2-ylidene)-4-benzyl-thiosemicarbazone,
1-(3-Allyl-4-oxo-thiazolidin-2-ylidene)-4-(thiophene-2-methyl)-thiosemicarbazone,
1-(3-Allyl-4-oxo-thiazolidin-2-ylidene)-4-(furan-2-methyl)-thiosemicarbazone,
1-(3-Allyl-4-oxo-thiazolidin-2-ylidene)-4-(tetrahydrofuran-2-methyl)-thiosemicarbazone,
1-(3-Allyl-4-oxo-thiazolidin-2-ylidene)-4-(2-picolyl)-thiosemicarbazone,
1-(3-Allyl-4-oxo-thiazolidin-2-ylidene)-4-phenylethyl-thiosemicarbazone,
1-(3-Allyl-4-oxo-thiazolidin-2-ylidene)-4-glycinyl ethyl ester thiosemicarbazone,
1(5,5-Dimethyl-3-methallyl-4-oxo-thiazolidin-2-ylidene)-4-glycinyl ethyl ester thiosemicarbazone,
1-(3-Allyl-4-oxo-thiazolidin-2-ylidene)-4-(2,2-dimethoxyethyl)-thiosemicarbazone,
[1-(3-Allyl-4-oxo-thiazolidin-2-ylidene)-2,4-dimethyl-thiosemicarbazone,]
1-(3-Allyl-4-oxo-thiazolidin-2-ylidene)-4-hydroxymethylphenyl-thiosemicarbazone,
1-(3-Allyl-4-oxo-thiazolidin-2-ylidene)-4-(3,4-methylene-dioxyphen-1-yl)-thiosemicarbazone,
1-(3-Allyl-4-oxo-thiazolidin-2-ylidene)-4-(propionic acidethyl ester-2-yl)-thiosemicarbazone,
1-(3-Allyl-4-oxo-thiazolidin-2-ylidene)-4-(2-methylpropionyl)-thiosemicarbazone,
1-(5,5-Dimethyl-3-methallyl-4-oxo-thiazolidin-2-ylidene)-4-benzoyl-thiosemicarbazone,
1-(3-Allyl-4-oxo-thiazolidin-2-ylidene)-4-(thiophene-2-carbonyl)-thiosemicarbazone,
1-(3-Allyl-4-oxo-thiazolidin-2-ylidene)-4-phenylacetyl-thiosemicarbazone,
1-(3-Allyl-4-oxo-thiazolidin-2-ylidene)-4-benzyloxycarbonyl-thiosemicarbazone,
[1-(3-Allyl-4-oxo-thiazolidin-2-ylidene)-2-acetyl-4-methyl-thiosemicarbazone,]
1-(3-Allyl-4-oxo-thiazolidin-2-ylidene)-4-p-hydroxyphenyl-thiosemicarbazone,
[1-(3-Allyl-4-oxo-thiazolidin-2-ylidene)-2-benzoyl-4-methyl-thiosemicarbazone,]
1-(3-Allyl-4-oxo-thiazolidin-2-ylidene)-4-allyloxycarbonyl-thiosemicarbazone, and
1-(3-Allyl-4-oxo-thiazolidin-2-ylidene)-4-cinnamoyl-thiosemicarbazone, or a pharmaceutically acceptable salt thereof.

6. A composition for the treatment of a disease of the rheumatoid type comprising a rheumatoid type disease treating effective amount of a compound of claim 1 or a pharmaceutically acceptable salt thereof together with a pharmaceutically acceptable carrier therefor.

7. A composition for the treatment of a disease of the rheumatoid type comprising a rheumatoid type disease treating effective amount of a compound of claim 3 or a pharmaceutically acceptable salt thereof together with a pharmaceutically acceptable carrier therefor.

8. A method of treating a disease of the rheumatoid-type in an animal in need thereof comprising administering to said animal a rheumatoid type disease treating effective amount of a compound of claim 1 or a pharmaceutically acceptable salt thereof.

9. A method of treating a disease of the rheumatoid-type in an animal in need thereof comprising administering to said animal a rheumatoid type disease treating effective amount of a compound of claim 5 or a pharmaceutically acceptable salt thereof.

* * * * *

UNITED STATES PATENT AND TRADEMARK OFFICE
CERTIFICATE OF CORRECTION

PATENT NO. : 5,344,842
DATED : September 6, 1994
INVENTOR(S) : Missbach

It is certified that error appears in the above-indentified patent and that said Letters Patent is hereby corrected as shown below:

In column 17, line 67 after "aryl" insert --or--

In column 18, lines 42-50, delete the entire meaning of $R_5$, "$R_5$ is phenyl....or phenylallyl" and insert --$R_5$ is phenyl, phenyl-lower alkyl, such as benzyl or phenylethyl, pyridyl-, thienyl-, pyrryl-, furyl-, pyrrolidinyl-, tetrahydrofuranyl- or tetrahydropyranyl-lower alkyl, such as pyridyl-, thienyl-, pyrryl- or furyl-, pyrrolidinyl-, tetrahydrofuranyl- or tetrahydropyranyl-methyl, $C_1$-$C_4$alkoxycarbonyl-$C_1$-$C_4$alkyl, such as methoxycarbonyl- or ethoxycarbonyl-methyl or -ethyl, or the group -C(=O)-$R_7$ wherein $R_7$ has the meaning of $R_6$ as defined for $R_4$ or is benzyl or phenylallyl,--

In column 20, line 4, after "thiosemicarbazone," insert --1-(3-Allyl-4-oxo-thiazolidin-3-ylidene)-4-phenoxycarbonyl-thiosemi-carbazone,--

In column 20, line 25, after "claim" delete "3" and insert --5-- lieu thereof.

Signed and Sealed this

Eighth Day of November, 1994

Attest:

BRUCE LEHMAN

Attesting Officer    Commissioner of Patents and Trademarks